(12) United States Patent
Tam et al.

(10) Patent No.: US 8,691,518 B2
(45) Date of Patent: Apr. 8, 2014

(54) SYSTEMS AND METHODS FOR PREDICTING RESPONSE TO MINOXIDIL FOR THE TREATMENT OF ANDROGENETIC ALOPECIA

(75) Inventors: Phillip Y. Tam, Rowland Heights, CA (US); Andy Ofer Goren, Newport Beach, CA (US)

(73) Assignee: Global Life Science Partners Limited, Central (HK)

( * ) Notice: Subject to any disclaimer, the term of this patent is extended or adjusted under 35 U.S.C. 154(b) by 141 days.

(21) Appl. No.: 13/245,783

(22) Filed: Sep. 26, 2011

(65) Prior Publication Data

US 2012/0077214 A1    Mar. 29, 2012

Related U.S. Application Data

(60) Provisional application No. 61/386,451, filed on Sep. 24, 2010.

(51) Int. Cl.
*C12Q 1/48* (2006.01)
*A01N 61/00* (2006.01)

(52) U.S. Cl.
USPC .................................. 435/15; 514/1

(58) Field of Classification Search
None
See application file for complete search history.

(56) References Cited

U.S. PATENT DOCUMENTS

| | | | |
|---|---|---|---|
| 4,849,347 A | 7/1989 | Familletti et al. | |
| 5,760,315 A * | 6/1998 | Verheijden et al. | 73/864.72 |
| 5,958,946 A | 9/1999 | Styczynski et al. | |
| 2011/0212167 A1 | 9/2011 | Ali et al. | |

FOREIGN PATENT DOCUMENTS

| CA | 2233961 A1 | 4/1997 |
|---|---|---|
| EP | 1307181 | * 11/2005 |

OTHER PUBLICATIONS

Anderson et al., Sulfation of minoxidil by multiple human cytosolic sulfotransferases., Chem Biol Interact. (1998), vol. 109(1-3), pp. 53-67.*
Frame et al., A Simple Colorimetric Assay for Phenotyping the Major Human Thermostable Phenol Sulfotransferase (SULT1A1) Using Platelet Cytosols, Drug Metabolism and Disposition (2000), vol. 28, pp. 1063-1068.*
Frame, L. T. et al., "A Simple Colorimetric Assay for Phenotyping the Major Human Thermostable Phenol Sulfotransferase (SULT1A1) Using Platelet Cytosols," Drug Metabolism and Disposition, vol. 28, No. 9, 2000, pp. 1063-1068.
Falany, C. N. et al., "Sulfation of Minoxidil by Human Liver Phenol Sulfotransferase," Biochemical Pharmacology, vol. 40, No. 5, 1990, pp. 1027-1032.
Johnson, G. A. et al., "Sulfation of Minoxidil by Human Platelet Sulfotransferase," Clinica Chimica Acta, vol. 169, 1987, pp. 217-228.
Buhl et al, "Minoxidil Sulfate is the Active Metabolite that Stimulate Hair Follicies", Journal of Investigative Dermatology, 1990, vol. 95, pp. 553-557.
PCT International Search Report and Written Opinion in International Application No. PCT/US12/57399, mailed on Feb. 21, 2013.
PCT Invitation to Pay Additional Fees and, Where Applicable, Protest Fee, in International Application No. PCT/US12/57399, mailed on Nov. 29, 2012.

* cited by examiner

*Primary Examiner* — Alexander Kim
(74) *Attorney, Agent, or Firm* — Nixon Peabody LLP; Khaled Shami

(57) ABSTRACT

Methods, processes, systems, and apparatuses are disclosed for predicting minoxidil response in the treatment of androgenetic alopecia based on colorimetric assay.

23 Claims, 2 Drawing Sheets

US 8,691,518 B2

SYSTEMS AND METHODS FOR PREDICTING RESPONSE TO MINOXIDIL FOR THE TREATMENT OF ANDROGENETIC ALOPECIA

CROSS-REFERENCE TO RELATED APPLICATIONS

This application claims priority to U.S. Provisional Application Ser. No. 61/386,451, filed on Sep. 24, 2010, titled "System and Method for Predicting Response to Minoxidil for the Treatment of Androgenetic Alopecia Based on a Rapid Colorimetric Assay."

TECHNICAL FIELD

The inventions described here relate to systems and methods for predicting minoxidil response in the treatment of androgenetic alopecia.

BACKGROUND

Hair loss is associated with a variety of psychological and social implications. Prior to starting any treatment it is advantageous to predict the course, severity, and treatment options of the disease. In the field of hair loss, very little scientific diagnostic tests are currently available, and there are few methods to predict treatment response.

Moreover, the hair loss industry is littered with dozens of products that claim to grow, improve, and replace hair. Unfortunately, few treatments have been scientifically demonstrated to work, and the few treatments that have undergone clinical trials often do not work equally for all patients.

Androgenetic alopecia has been successfully treated in men by the U.S. Food &

Drug Administration ("FDA") approved medications minoxidil (marketed as Rogaine™ or Regame™). Minoxidil has also been approved by the FDA for treatment of female hair loss; however, for most women minoxidil is only marginally successful at retaining existing hair. Some men for whom minoxidil is less effective have been successfully treated with finasteride; however, the same cannot be said of females for whom minoxidil is ineffective. Studies have thus far failed to show the effectiveness of finasteride in the treatment of female androgenetic alopecia.

There are significant differences between male androgenetic alopecia and female androgenetic alopecia. Apart from the different baldness patterns, male and female alopecia follow a different mechanism. In men, alopecia is related to the normal high androgen levels in males, combined with an underlying sensitivity of the hair roots to androgens. Women, however, have roughly 10 times lower androgen levels than men, and the absolute amount of androgen is a less significant factor than the increased sensitivity of the hair roots to androgens.

Among various individuals, whether male or female, there is a broad variability in the response of different people to various hair loss treatments. This variability is presumed to be a result of genetic factors contributing to variable enzyme activity in the follicles, making a one-size-fits-all approach difficult to achieve. It would therefore be advantageous to be able to have an effective diagnostic and treatment method where patients could be selected and treated on the basis of criteria such as enzyme activity, which would identify some people as being likely to benefit from treatment by minoxidil and other drugs, while identifying other individuals in which treatment is not likely to be effective.

BRIEF SUMMARY

The inventions described here relate to systems and methods for predicting minoxidil response in the treatment of androgenetic alopecia, which in one embodiment may be based on a colorimetric assay. Various embodiments are possible, a number of which are exemplified here. In particular, variations in hair follicle minoxidil sulfotransferase activity may be used to predict the efficacy of minoxidil for the treatment of androgenetic alopecia.

In one embodiment of the present disclosure, there is provided a method for selecting a treatment for a subject suffering from androgenetic alopecia, comprising obtaining a sample of one or more hair follicles, or a scalp biopsy, from the subject; performing an assay to measure minoxidil sulfotransferase activity in the sample, thereby generating an activity value indicative of the minoxidil sulfotransferase activity level in the sample; comparing the activity value to one or more standardized activity values, each standardized activity value representing either high or low expected minoxidil response for hair re-growth or retention for a class of patients including the subject, thereby producing an indication of either high or low expected minoxidil response for hair re-growth or retention for the subject at a particular dosage of minoxidil; and presenting the indication to the subject.

In another embodiment, there is provided a composition of matter for performing an assay comprising about 30 to about 70 mM potassium phosphate buffer (pH 6.5); about 3 to about 7 mM magnesium chloride; about 15 to about 25 µM adenosine 3',5'-diphosphate (PAP) or adenosine 3'-phosphate, 5'-phosphosulfate (PAPS); about 3 to about 7 mM p-nitrophenyl sulfate; and about 0.07 to about 0.13 mM minoxidil.

In another embodiment, there is provided a kit comprising a transparent container with a lid, comprising the above composition for performing an assay; a buffer container comprising about 0.20 M to about 0.30 M Tris-HCl, pH 8.7; and means for mixing the contents of the buffer container with the contents of the apparatus.

BRIEF DESCRIPTION OF THE DRAWINGS

The accompanying drawings, which are incorporated into this specification, illustrate one or more exemplary embodiments of the inventions disclosed herein and, together with the detailed description, serve to explain the principles and exemplary implementations of these inventions. One of skill in the art will understand that the drawings are illustrative only, and that what is depicted therein may be adapted based on the text of the specification or the common knowledge within this field.

In the drawings, where like reference numerals refer to like reference in the specification.

DETAILED DESCRIPTION

Figure 1:
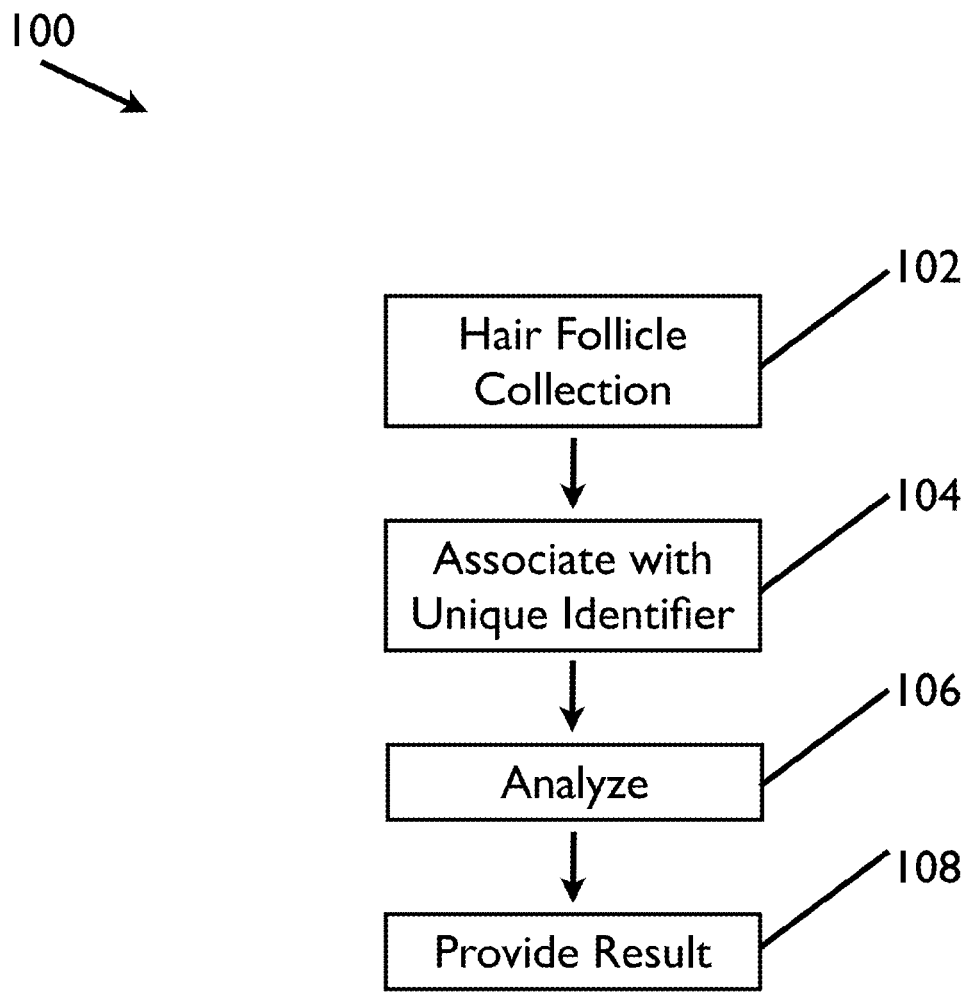
FIG. 1 is a flowchart showing a method of analyzing one or more hair follicles and providing a result.

Various example embodiments of the present inventions are described herein in the context of a therapy for androgenetic alopecia.

The description herein is provided in the context of a therapy for androgenetic alopecia. Those of ordinary skill in the art will realize that the following detailed description is illustrative only and is not intended to be in any way limiting. Other embodiments will readily suggest themselves to such skilled persons having the benefit of this disclosure. Reference will now be made in detail to implementations as illustrated in the accompanying drawings. The same reference indicators will be used throughout the drawings and the following detailed description to refer to the same or like parts.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

Androgenetic alopecia is extremely common, affecting approximately 60% of men and over 50% of females by the age of 60. Currently, there are two FDA approved medications for the treatment of androgenetic alopecia, finasteride and minoxidil. However, finasteride therapies that are successful at hair re-growth and maintenance in males have failed to show significant improvement in females. Therefore, minoxidil is currently the only FDA approved medication for female hair loss. Further, for minoxidil therapy to be effective it often must be used for a prolonged period of time without knowing if it is effective. One aim of this invention is to screen patients that will respond best to minoxidil therapy and thereby provide personalized effective therapy for hair loss.

The invention is based in part on the discovery that minoxidil requires biochemical activation by minoxidil sulfotransferase to form the active minoxidil sulfate metabolite. The exact mechanism of action for minoxidil based treatment of androgenetic alopecia is not completely understood. However, in vitro studies have demonstrated that minoxidil sulfate is the active metabolite of minoxidil. Response to minoxidil for the treatment of androgenetic alopecia has been associated with differences in scalp sulfotransferase activity. Therefore, a subject with a high level of minoxidil sulfotransferase activity will generate more minoxidil sulfate, and therefore will likely have a good response to minoxidil for the treatment of androgenetic alopecia. On the other hand, a subject with a low level of minoxidil sulfotransferase activity will not generate much minoxidil sulfate, and will likely have a poor response to minoxidil for the treatment of androgenetic alopecia.

Clinical trials with minoxidil for the treatment of androgenetic alopecia have shown statistically significant results for maintenance and growth of hair. Several studies have demonstrated the level of minoxidil sulfotransferase activity is significantly greater in patients responding to minoxidil for the treatment of androgenetic alopecia. As described herein, the assessment of hair re-growth is based on one or more of the following parameters: patient self assessment, physician assessment using a standardized scale, global photography assessment, hair diameter measurement, average hair length measurement, average hair diameter measurement, and hair weight measurements. The current inventions provide a method of using biochemical variations in minoxidil sulfotransferase activity as a drug response marker for minoxidil treatment of androgenetic alopecia. Based on the minoxidil sulfotransferase activity level, the method disclosed herein allows a physician or the patient to select the appropriate treatment and dosage thereof for the treatment of androgenetic alopecia.

In accordance with one approach described herein, a patient's hair follicle sample may be obtained. Preferably, at least two hair follicles may be obtained, so that if only one is analyzed, there will be at least one backup if needed.

The patient's hair follicle sample may be subjected to a colorimetric assay to determine the level of minoxidil sulfotransferase activity. A patient's hair follicle sample (from 1 to n hair follicles) may be placed in a reaction mixture containing about 50 mM potassium phosphate buffer (pH approximately 6.5), about 5 mM magnesium chloride, about 20 µM adenosine 3',5'-diphosphate (PAP) or adenosine 3'-phosphate,5'-phosphosulfate (PAPS), about 5 mM p-nitrophenyl sulfate and about 0.1 mM minoxidil.

In one embodiment this reaction may take place in a transparent container with a lid or other opening in which the hair follicle samples may be inserted. In one non-limiting example, the total amount of liquid in the assay container may be about 0.2 ml.

As part of the above reaction, it is understood that in the presence of minoxidil sulfotransferase activity, p-nitrophenyl sulfate is converted to the colorimetric p-nitrophenolate.

The reaction may be mixed and then incubated for approximately 4 to 16 hours at 37° C. depending on the number of hair follicles used in the assay. Mixing may be by any mixing means known in the art, including shaking the container. Where a shorter incubation time is required for a greater number of hair follicles. In one embodiment, an assay that uses one hair follicle may be incubated for approximately 16 hours. In another embodiment, an assay that uses two hair follicles may be incubated for approximately four hours.

After sample incubation, the reaction may be stopped by addition of about 1/10th volume of approximately 0.25 M Tris-HCl buffer, pH 8.7, and mixed. The pH may vary, in one embodiment between 8.5 to 9.0. Especially if the assay is performed or sold as part of a kit, the basic buffer may be provided as a separate container for pouring into the assay reaction container. In another embodiment, the basic buffer may be provided in a pre-loaded syringe, to be injected into the main reaction container at the appropriate time, either by manually pushing a plunger, or by some automatic or computerized control.

The absorbance at about 405 nm may then be read with a spectrophotometer or compared to a reference color card with a range of intensities corresponding to minoxidil sulfotransferase activity. Patients with a relatively high level of sulfotransferase activity will have a relatively strong colorimetric readout, resulting in a relatively significant color change. In comparison, patients with a relatively low level of sulfotransferase activity will have a relatively weak colorimetric readout, and correspondingly a relatively minimal color change. Patients with a strong colorimetric assay response would be expected to respond to minoxidil for hair re-growth or retention. Whereas, patients with a weak colorimetric assay response would be expected to have a poor response to minoxidil.

In yet another embodiment, the result from a patient's hair follicle colorimetric assay is used to determine an optimal treatment regime. Including, modifying the concentration and/or frequency of minoxidil therapy to suit the patient's minoxidil sulfotransferase activity. Furthermore, if a patient is unlikely to respond to minoxidil, finasteride may be recommended as an alternative to minoxidil.

With reference to FIG. 1, a method 100 as described herein includes, at 102, collection of a hair follicle sample from a subject. Then, at 104, the hair follicle sample may be coded with a unique identifier, for instance to protect privacy and facilitate handling. At 106, the hair follicle sample may be analyzed as described above. The analysis can be performed using the colorimetric assay described herein. The results of the analysis may then be provided to the subject or to the caregiver of the subject, at 108. The results of the analysis, each associated with its unique identifier, can be transmitted to a computer system that may include a Web-based server that is accessible, with proper authentication for instance using the unique identifier, by the subject or caregiver. The result, in addition to providing an indication of the likelihood that the patient will respond to 2%, 5% or greater minoxidil for the treatment of androgenetic alopecia, may also include a prediction of the dosage required and daily frequency of treatment by comparing a patient's minoxidil sulfotransferase activity level to a reference database.

Figure 2:
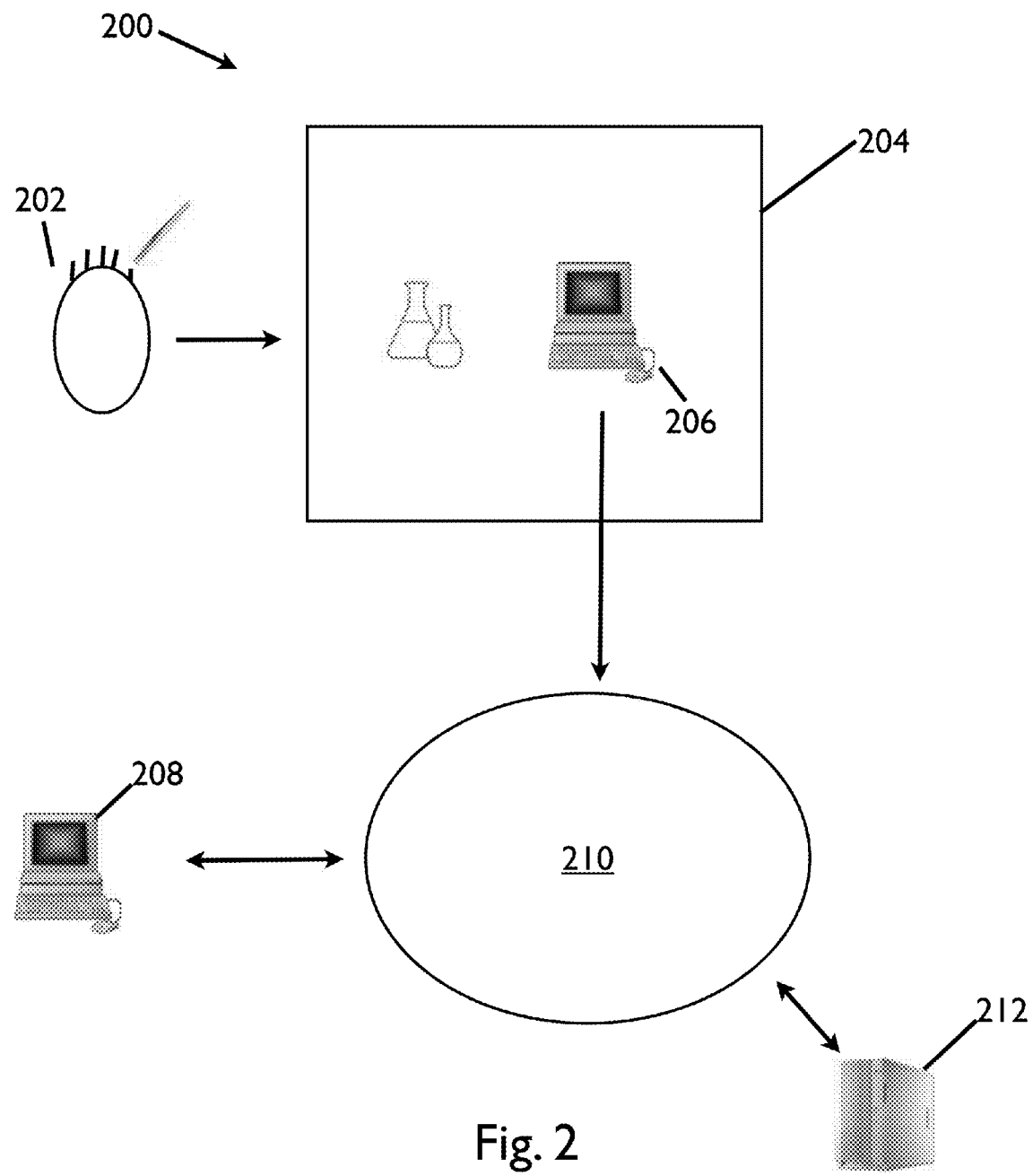
FIG. 2 shows an example of a computerized system for conducting or analyzing an assay to test hair follicles and providing a result.

FIG. 2 schematically shows a system 200 for implementing the above procedure. A sample 202 of hair follicle from a subject is sent to a lab 204. An analysis of the sample in accordance with one or more of the afore-mentioned procedures is then conducted. Results of the analysis are for example compared with a database to generate an indication of the likelihood that the patient will respond to minoxidil for the treatment of androgenetic alopecia. The database may be dynamic in nature, continuously updated for statistical adaptation based on past minoxidil treatment and response thereto, so that the database can adapt, or learn, from the patient pool and treatments over time, and in this manner become a better predictor of the likelihood of responders to the drug treatment. The database, or other entity or circuit or module capable of the adaptive scheme herein described, may reside in computer system 206 or separately therefrom. The outcome of the comparison and analysis can be forwarded to the subject's or caregiver's computer system 208, for example electronically by way of a network, such as the Internet, 210. Alternatively or in addition, the outcome of the comparison and analysis can be stored on a server 212 for accessing remotely by the subject or caregiver following proper authentication that may require reference to the unique identifier to preserve privacy.

It may also be possible to use a neural network to implement the system and method, to predict the likelihood that the patient will respond to minoxidil for the treatment of androgenetic alopecia based on the patient's minoxidil sulfotransferase activity profile. According to such an approach, for predicting the likelihood of response to the drug treatment can include (a) constructing an N-layer neural network, and (b) training the neural network with a data set of patients' outcomes to treatment with minoxidil for androgenetic alopecia along with the patients' minoxidil sulfotransferase activity profiles, (c) obtaining a hair follicle sample from the subject (d) generating a minoxidil sulfotransferase activity profile from the sample, the profile being a function of values associated with a prescribed set of minoxidil sulfotransferase activity levels; (e) inputting the subjects minoxidil sulfotransferase activity profile into the neural network; (f) obtaining a value or set of values from the neural network indicative of the patient's expected outcome (respondent) to the drug treatment at a single or multiple dosages; and (g) providing the patient the drug treatment at the recommended dosage.

The above are exemplary modes of carrying out the invention and are not intended to be limiting. It will be apparent to those of ordinary skill in the art that modifications thereto can be made without departure from the spirit and scope of the invention as set forth in the following claims.

What is claimed is:

1. A method for selecting a treatment for a human subject suffering from androgenetic alopecia, comprising:
obtaining a sample from the human subject, comprising one or more hairs that have been plucked from the human subject, said hairs comprising one or more hair follicles;
performing a colorimetric assay to measure minoxidil sulfotransferase activity in the sample, thereby generating an activity value indicative of the minoxidil sulfotransferase activity level in the sample, wherein the assay comprises the step of placing the sample in a reaction mixture comprising an indicator dye and minoxidil, and wherein during the assay, the indicator dye undergoes a color change that correlates with the amount of minoxidil sulfotransferase activity level in the sample, and wherein the activity value correlates with said color change;
comparing the activity value to one or more standardized activity values, each standardized activity value representing either high or low expected minoxidil response for hair re-growth or retention for a class of patients including the subject, thereby producing an indication of either high or low expected minoxidil response for hair re-growth or retention for the subject at a particular dosage of minoxidil; and
presenting the indication to the human subject.

2. The method of claim 1, wherein the indication is of high expected minoxidil response for hair re-growth or retention, and the particular dosage of minoxidil is selected from the group consisting of approximately 2% topical solution, approximately 5% topical solution, approximately 2% topical foam, approximately 5% topical foam, approximately 2.5 mg tablet, and approximately 5 mg tablet.

3. The method of claim 1, wherein the assay further comprises the steps of:
placing the sample in a reaction mixture containing about 50 mM potassium phosphate buffer with pH between about 6.5 and about 8.0, about 5 mM magnesium chloride, about 20 µM adenosine 3',5'-diphosphate (PAP) or adenosine 3'-phosphate, 5'-phosphosulfate (PAPS), about 5 mM p-nitrophenyl sulfate and about 0.1 mM minoxidil;
mixing the reaction mixture which contains the sample, such that a reaction is initiated;
incubating the sample within the reaction mixture for a predetermined length; and
stopping the reaction.

4. The method of claim 3, wherein the potassium phosphate buffer has a pH of about 8.0.

5. The method of claim 3, wherein a basic buffer of about 0.25 M Tris-HCl, pH approximately 8.7 is added to the reaction mixture to quench the assay and improve sensitivity of the assay.

6. The method of claim 3, wherein the reaction mixture is incubated for about 4 to about 16 hours at about 37° C.

7. The method of claim 3, wherein the sample within the reaction mixture is incubated at room temperature.

8. The method of claim 3, wherein the reaction mixture is incubated above room temperature to increase dye turnover and the signal strength of the colorimetric assay.

9. The method of claim 3, wherein the reaction mixture is packaged in a capsule and dissolved in a solution along with the sample.

10. The method of claim 1, wherein the one or more standardized values are one or more minoxidil sulfotransferase activity levels at which a statistical sample of other subjects show either high or low minoxidil response for hair re-growth or retention at the particular dosage of minoxidil.

11. The method of claim 1, wherein the step of presenting comprises sending an electronic signal.

12. The method of claim 1, wherein the indicator dye is p-nitrophenyl sulfate.

13. The method of claim 1, wherein the colorimetric assay uses 2-naphthol as a substrate, to improve the sensitivity or specificity of the assay.

14. The method of claim 1, wherein the sample consists of one hair comprising one hair follicle that has been plucked from the human subject.

15. The method of claim 1, wherein the reaction time for the assay is inversely correlated with the number of hair follicles in the reaction.

16. The method of claim 1, wherein the human subject with high minoxidil sulfotransferase activity is prescribed a low dose of minoxidil and/or a decrease in the frequency of minoxidil application.

17. The method of claim 1, wherein the human subject with low minoxidil sulfotransferase activity is prescribed a high dose of minoxidil and/or an increase in the frequency of minoxidil application.

18. The method of claim 17, wherein the human subject with low minoxidil sulfotransferase activity is prescribed a stabilized form of minoxidil sulfate in the form of a cream, solution and/or gel.

19. The method of claim 18, wherein minoxidil sulfate is stabilized in liposomes or microencapsulation.

20. The method of claim 1, where the assay includes a positive (reference) and negative (blank) control to compare to the sample.

21. The method of claim 1, wherein said color change is visually discernible, and wherein said assay is performed in a transparent container.

22. The method of claim 21, wherein said generating an activity value is performed by comparing the discernible color after the color change to a reference color card.

23. The method of claim 1, wherein said colorimetric assay is performed in a transparent container, and generating an activity value is performed by measuring the absorbance at approximately 405 nm with a spectrophotometer.

* * * * *